US010204281B2

(12) United States Patent
Waser (10) Patent No.: US 10,204,281 B2
(45) Date of Patent: Feb. 12, 2019

(54) MULTI-CHAMBER ANALYSIS DEVICE AND METHOD FOR ANALYZING

(71) Applicant: Roche Molecular Systems, Inc., Pleasanton, CA (US)

(72) Inventor: Patrick Waser, Lucerne (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/714,223

(22) Filed: Sep. 25, 2017

(65) Prior Publication Data

US 2018/0089521 A1 Mar. 29, 2018

(30) Foreign Application Priority Data

Sep. 29, 2016 (EP) .................................... 16191425

(51) Int. Cl.
*G06K 9/00* (2006.01)
*G06K 9/20* (2006.01)
(Continued)

(52) U.S. Cl.
CPC ......... *G06K 9/2063* (2013.01); *G01N 21/253* (2013.01); *G01N 33/4875* (2013.01);
(Continued)

(58) Field of Classification Search
CPC ......... G06T 7/246; G06T 7/73; G06T 3/4038; G06T 2207/20212; G06T 2210/41;
(Continued)

(56) References Cited

U.S. PATENT DOCUMENTS 3,527,074 A 9/1970 Guillot
4,745,484 A 5/1988 Drexler et al.
(Continued)

FOREIGN PATENT DOCUMENTS

EP 0216923 B1 6/1993
WO WO2006031537 3/2006

OTHER PUBLICATIONS

EP16191425.4 Search Report.

*Primary Examiner* — Shefali D Goradia
(74) *Attorney, Agent, or Firm* — Pamela C. Ancona (57) ABSTRACT

A method for analyzing a multi-chamber plate (110) is disclosed. The method comprises the following steps:
  displacing (110) at least one imaging device (114) and the multi-chamber plate (110) relative to each other along at least one axis;
  imaging (130) at least one first partial image of at least one first partial region (132) of the multi-chamber plate (110) and at least one second partial image of at least one second partial region (134) of the multi-chamber plate (110), wherein the first partial region (132) and the second partial region (134) are one or both of adjacent or overlapping partial regions of the multi-chamber plate (110);
  adjusting (138) an orientation of one or both of the multi-chamber plate (110) or the imaging device (114) such that at least one contour line (138) is observable in both the first partial region (132) and the second partial region (134);
  forming (140) at least one composite image from the first partial image and the second partial image by matching the first partial image and second partial image by using the contour line (138).

12 Claims, 6 Drawing Sheets

(51) Int. Cl.
*G06K 9/32* (2006.01)
*G06T 7/73* (2017.01)
*G06K 9/46* (2006.01)
*G06T 7/246* (2017.01)
*G06K 9/48* (2006.01)
*G01N 33/487* (2006.01)
*G06T 3/40* (2006.01)
*G01N 21/25* (2006.01)

(52) U.S. Cl.
CPC ......... *G06K 9/3208* (2013.01); *G06K 9/3216* (2013.01); *G06K 9/4609* (2013.01); *G06K 9/48* (2013.01); *G06T 3/4038* (2013.01); *G06T 7/246* (2017.01); *G06T 7/73* (2017.01); *G06T 2207/20212* (2013.01); *G06T 2210/41* (2013.01)

(58) Field of Classification Search
CPC ............. G01N 21/253; G01N 33/4875; G06K 9/3208; G06K 9/3216; G06K 9/4609; G06K 9/48; G06K 9/2063
See application file for complete search history.

(56) References Cited

U.S. PATENT DOCUMENTS

| | | | |
|---|---|---|---|
| 4,963,724 A | 10/1990 | Neumann | |
| 7,834,968 B2 * | 11/2010 | Tsuchiya | G02F 1/1395 349/122 |
| 9,216,065 B2 * | 12/2015 | Cohen | A61B 5/0044 |
| 2005/0211874 A1 | 9/2005 | Takeyama et al. | |
| 2010/0068822 A1 | 11/2010 | Heydenhauss et al. | |
| 2011/0001036 A1 | 1/2011 | Stallinga et al. | |
| 2011/0071055 A1 | 3/2011 | Belgrader et al. | |
| 2013/0280748 A1 | 10/2013 | Gebetsroither | |
| 2015/0278625 A1 | 10/2015 | Finkbeiner et al. | |
| 2016/0082502 A1 * | 3/2016 | Appleby | B22C 9/04 164/369 |

* cited by examiner

MULTI-CHAMBER ANALYSIS DEVICE AND METHOD FOR ANALYZING

CROSS-REFERENCE TO RELATED APPLICATIONS

The present application claims the benefit of priority under 35 U.S.C. § 119(a) of 16191425.4, filed Sep. 29, 2016. Reference is also made to EP16183569.9, filed Aug. 10, 2016; EP16002058.2 and EP16002057.4, each filed Sep. 23, 2016; and EP16191771.1, EP16400044.0; EP16191811.5, each filed Sep. 30. The disclosures of each of these applications are incorporated herein by reference in their entireties.

FIELD OF THE DISCLOSURE

The disclosure relates to a multi-chamber plate analysis device and a method for analyzing a multi-chamber plate. Multi-chamber plates and methods according to the disclosure may particularly be used in the field of in-vitro diagnostics (IVD), for example for analyzing samples of a human body, like blood, urine, saliva, interstitial fluid or other body fluids.

BACKGROUND

In the field of IVD, multi-chamber plates have become a widely used tool. Thus, various geometries for chamber plates and methods for filling them are known. Multi-chamber plates may comprise a matrix of wells, for example thousands of micro wells or nano wells, defining the chambers. Reading out such small structures on multi-chamber plates is challenging.

Several methods exist for reading out small structures, for example warps, bends in surfaces of labels, cards or other data storage media. For example, U.S. Pat. No. 4,745,484 A describes a method and apparatus for reading data in a data field on a data surface of a storage medium in which the data surface may be nonplanar and depth wise regions of the data field are brought one-by-one into the region of focus of a CCD area array. A set of partial images is formed which are then merged together into a composite image of the data field to be read. The storage medium is disposed on a vacuum chuck. Imaging optics, such as a single lens, zoom lens or lenticular array images regions of the data surface which are within a region of focusing onto the CCD area array. A piezoelectric device or a linear variable differential transformer serve as a Z-axis focusing element which responds to oscillator or electrical control signals to change the relative distance between the CCD area array and a reference plane of the data surface. The partial images formed are either merged in semiconductor memory by a processor or are merged automatically by the CCD area array.

In such methods, data spots are stored at uneven depth over the surface of the medium and relative to a focal plane of the optical detection system of a reader. A major case of this unevenness is that the data surface has tilts, warps or bends relative to an ideal or "target" surface parallel to the focal plane. An ensuing problem is that some data spots are out of the target plane resulting in errors in reading the data. Various auto-focus mechanisms, usually servo-controlled, are known, which control a position of a lens to bring the data spot into sharp focus of a detector. For example, EP 0 216 923 B1 describes a method of inspecting a surface illuminated with light comprising the steps of: illuminating the surface with light, imaging light from said surface reflected from a screen or other member and re-reflected from said surface to form an image of said surface on an image sensor, and determining from said image detected or recorded by said image sensor, the condition of said surface.

U.S. Pat. No. 4,963,724 A describes an apparatus for producing an optical image contrast which may be used in a microscope. Specifically, the apparatus is based on the Moiré effect and uses two screens or gratings which are rotated simultaneously at different angular velocities in order to increase the depth of focus and resolution achievable with conventional systems.

DE 3 527 074 A1 describes an arrangement for determining the surface contour of objects by means of the moiré technique and is intended, in particular, for use in stereomicroscopes, particularly in surgical microscopes, or else in similar systems for inspection. The aim is for the moiré fringes that are generated for determining the surface contour to be displaced in a measurable fashion without changing the position of the object, and in addition it is to be possible for the vertical resolution to be improved. A surgical microscope with an assigned projection system for a grid and with a projection or reference grid that is located in the observation beam path of the surgical microscope and in the beam path of the projection system and is intended for producing a morié pattern has a tiltable, plane-parallel glass plate arranged downstream of the projection grid in the projection beam path, as a result of which the relative position of grid and reference grid is altered and the morié pattern or contour lines are measurably displaced. The observability can be substantially increased by periodic tilting of the plane-parallel plate, and the number of contour lines can be increased by pulsed operation of the illuminating device of the projection system and periodic tilting, synchronized with the light pulses, of the plane-parallel plate, and the contour lines can be displaced in a pinpointed fashion.

The methods for reading out small structures, however, exhibit some significant disadvantages and shortcomings. Thus, such methods are complicated. Furthermore, such methods are not suitable for multi-chamber plates. For example such methods require fiducials which need space which cannot be used for samples. Autofocus techniques, however, may lead to the necessity that each field of view needs to be captured several times, each with different foci, in order to determine enough wells sharply to assign individual coordinates. At readout of thousands of micro wells or nano wells, it must be ensured that each individual well is counted and none of them double. This is, however, challenging if the field of view of an optical system cannot cover the multi-chamber plate such that the optical system images only partial images of the multi-chamber plate. In this case stitching of fields of view, in particular of the partial images, is necessary and columns and/or rows need to be counted in order to know the exact displacement during stitching of partial images. Furthermore, in contrast to data storage media like cards etc. the multi-chamber plate may be bent and warped during thermal cycling.

It is therefore an objective of the present disclosure to provide a multi-chamber plate analysis device and a method for analyzing a multi-chamber plate, which at least partially overcome the shortcomings of devices and methods known from prior art. Specifically, devices and methods for simple and reliable readout of multi-chamber plates should be provided.

SUMMARY

The disclosure provides a device and methods for analyzing a multi-chamber plate. In a particular embodiment, the disclosure contemplates a method including the following steps:

a) displacing at least one imaging device and the multi-chamber plate relative to each other along at least one axis;

b) imaging at least one first partial image of at least one first partial region of the multi-chamber plate and at least one second partial image of at least one second partial region of the multi-chamber plate, wherein the first partial region and the second partial region are one or both of adjacent or overlapping partial regions of the multi-chamber plate;

c) adjusting an orientation of one or both of the multi-chamber plate or the imaging device such that at least one contour line is observable in both the first partial region and the second partial region; and d) forming at least one composite image from the first partial image and the second partial image by matching the first partial image and second partial image by using the contour line.

BRIEF DESCRIPTION OF THE FIGURES

For a more complete understanding of the present disclosure, reference is made to the following description of specific embodiments made in connection with accompanying drawings. The features disclosed therein may be realized in an isolated way or in combination with other features. The disclosure is not restricted to the embodiments. Identical reference numbers in the drawings refer to identical and/or functionally similar elements, which correspond to each other with regard to their functions.

DETAILED DESCRIPTION

In a first aspect of the present disclosure, a method for analyzing a multi-chamber plate is disclosed. The method comprises the following steps:

displacing at least one imaging device and the multi-chamber plate relative to each other along at least one axis;

imaging at least one first partial image of at least one first partial region of the multi-chamber plate and at least one second partial image of at least one second partial region of the multi-chamber plate, wherein the first partial region and the second partial region are one or both of adjacent or overlapping partial regions of the multi-chamber plate;

adjusting an orientation of one or both of the multi-chamber plate or the imaging device such that at least one contour line is observable in both the first partial region and the second partial region;

forming at least one composite image from the first partial image and the second partial image by matching the first partial image and second partial image by using the contour line.

The method steps may be performed in the given order or may be performed in a different order. Further, one or more additional method steps may be present which are not listed. Further, one, more than one or even all of the method steps may be performed repeatedly.

As used herein, the term "multi-chamber plate" refers to an arbitrarily formed element having a plurality of chambers. Examples of multi-chamber plates may be fluidic chips being partially or integrally made of glass, plastics, semiconductor materials, ceramic materials or metallic materials, having a fluid structure. Fluidic structures may be made, e.g., by etching, molding, machining, laser engraving, lithographic techniques or by other methods. The whole multi-chamber plate or parts of it may be made of transparent materials, but may also be partially or completely opaque. The multi-chamber plate may have a channel system for filling the chambers with at least one sample fluid. The sample fluid may be or may comprise any fluid medium, i.e. at least one liquid medium and/or at least one gaseous medium. Particularly, the sample fluid may comprise all kinds of body fluids, like blood, interstitial fluid, urine or saliva, or parts thereof. The multi-chamber plate according to this disclosure can particularly be used for analytical purposes. The multi-chamber plate may be used in the field of IVD, as described above.

The multi-chamber plate may comprise a plurality of wells. The multi-chamber plate may be a micro-well plate or a nano-well plate. The multi-chamber plate may comprise at least one array of chambers. In particular, the multi-chamber plate may comprise an array of wells. The chambers may comprise chamber walls. For example, a well may have four chamber walls and may have a rectangular or quadratic base area. However, other base areas are possible.

The multi-chamber plate may comprise a matrix with columns and rows formed by chamber walls. As used herein, the term "matrix" generally refers to an arrangement of a plurality of elements in a predetermined geometrical order. The matrix specifically may be or may comprise a rectangular matrix having one or more rows and one or more columns. The rows and columns specifically may be arranged in a rectangular fashion. However, other arrangements are feasible, such as nonrectangular arrangements.

The method comprises displacing the at least one imaging device and the multi-chamber plate relative to each other along at least one axis. As used herein, the term "displacing" refers to a continuous or non-continuous movement of one or both of the imaging device and the multi-chamber plate relative to each other along at least one axis. The imaging device and/or the multi-chamber plate may be displaced along one axis, or along more than one axis. The multi-chamber plate may have a first end and a second end. An x direction may be defined as direction from the first end to the second end. A length of the multi-chamber plate may be a distance from the first end to the second end. Particularly one or both of the imaging device and the multi-chamber plate may be displaced relative to each other along one axis, in particular along the x-axis. A y-axis may be perpendicular to the x-axis, in particular along a width of the multi-chamber plate. In case of a flat multi-chamber plate, the rows of the matrix may be arranged equidistantly along the y-axis and parallel to the x-axis and the columns may be arranged equidistantly along the x-axis and parallel to the y-axis. A z-axis may be perpendicular to an xy plane The multi-chamber plate may comprise an essentially flat element comprising the plurality of chambers. The chambers may be located in one and the same plane. The essentially flat element may comprise a surface. The term "essentially flat" refers to the condition of an orientation in the xy plane. The essentially flat element may be planar within the xy plane, with a tolerance of e.g. ±20° or less, particularly a tolerance of ±10° or less, more particularly a tolerance of ±5° or less. In particular, the surface of the essentially flat element may be planar within the xy plane, with a tolerance of e.g. ±20° or less, particularly a tolerance of ±10° or less, more particularly a tolerance of ±5° or less. The flat element, and in particular the surface, may be bent and/or warped during thermal cycling such that deviations from the planar design occur.

As used herein, the term "imaging device" generally refers to a device or a combination of a plurality of devices configured for imaging at least one part of the multi-chamber plate. As further used herein, the term "imaging" generally refers to continuously or subsequently one or more of detecting, mapping, recoding, taking an image of at least one partial region of the multi-chamber plate. The imaging device may comprise at least one sensor, in particular at least one optical sensor. The sensor may be formed as a unitary, single device or as a combination of several devices. The imaging device may comprise at least one optical system. The optical system may comprise at least one optical element selected from the group of: at least one detector, at least one lens; at least one lens system. The imaging device may be adapted to monitor a movement of the multi-chamber plate along the axis, in particular continuously. For example, the imaging device may comprise a camera, e.g. a video-camera.

The method comprises imaging the first partial image of the first partial region of the multi-chamber plate and the second partial image of the second partial region of the multi-chamber plate. The imaging device may have a field of view smaller than an extension of the multi-chamber plate along the axis. As used herein, the term "extension along the axis" refers to the length of the multi-chamber plate, i.e. in case of a flat multi-chamber plate a distance from first end to the second end. The extension of the multi-chamber plate may be two, three or more times larger than the field of view such that the imaging device may be adapted to image parts of the multi-chamber plate. The denotation as "first" and "second" are solely used in order to enable differentiation between the "partial regions" or "partial images," respectively, and do not imply any order of the "partial regions" or "partial images." As used herein, the term "partial region" generally refers to parts, regions or areas of the multi-chamber plate, in particular parts of the multi-chamber plate having an equal width but smaller length than the multi-chamber plate. Partial regions, in particular a length in the x direction, may be defined by the displacement and the field of view of the imaging device. Each partial region may have a center, wherein the centers of the first partial region and the second partial region have different x-coordinates. The first partial region and the second partial region may be adjacent subsequent regions along the x axis. The first partial region and the second partial region may be neighboring partial regions. The first partial region and the second partial region may overlap. The first and second partial regions may be imaged without changing a focal length of the imaging device. As further used herein, the term "partial image" generally refers to an image of the partial region. The method may comprise imaging subsequent partial regions of the multi-chamber plate. The method may comprise imaging the entire multi-chamber plate. The imaging device may be adapted to image the entire multi-chamber plate by imaging a plurality of partial regions.

The method comprises adjusting the orientation of one or both of the multi-chamber plate or the imaging device such that at least one contour line is observable in both the first partial region and the second partial region. As used herein, the term "adjusting" generally refers to one or more of aligning, shifting, tilting, changing, twisting one or both of the orientation of the multi-chamber plate or the orientation of imaging device. The imaging device may comprise at least one sensor having at least one sensor surface. Adjusting the orientation of the image device and/or of the multi-chamber plate may comprise adjusting a spatial orientation of the sensor surface and the multi-chamber plate relative to each other, in particular changing at least one spatial angle between the sensor surface and the multi-chamber plate. As used herein, the term "orientation" refers to an angular position in space, in particular to a spatial angle between the imaging device and the multi-chamber plate. For example, the multi-chamber plate and/or the imaging device may be tilted relative to each other by no more than 20°, particularly of no more than 10°, more particularly of no more than 5°.

For example, the multi-chamber plate may be tilted within a depth of field of the imaging device. As used herein, the term "depth of field," also called focus range, generally refers to a distance from the imaging device at which a point-like object produces a point image. At this distance the point-like object is focused, wherein at any other distance it is defocused. The multi-chamber plate may be tilted precisely within and slightly beyond the depth of field. Additionally or alternatively, the imaging device may be tilted such that the multi-chamber plate is precisely within and slightly beyond the depth of field. The multi-chamber plate may be tilted and/or may be within the depth of field of the imaging device such that the contour line may be precisely focused and/or acceptably sharp. As used herein, the term "contour line" generally refers to points of essentially equal height with respect to the xy plane. In particular, the points of the contour line may have the essentially equal distance from the imaging device. As used herein, the term "essentially equal height" and "essentially equal distance" generally refer to equal height and distance within a tolerance of ±10% or less of the depth of field, particularly a tolerance of ±5% or less of the depth of field, more particularly a tolerance of ±2% or less of the depth of field.

The contour line may be a curved contour line or a straight contour line. The contour line may be continuous. In particular the contour line may be continuous in a transition or a transition region or an overlapping region of the first and second partial regions. Specifically, the contour line may have no jumps in the transition region or the overlapping region of the first and second partial regions. The contour line may extend in both the first and the second partial regions. The multi-chamber plate may have the first end and the second end, wherein the contour line may extend from the first end to the second end. The contour line may extend in two adjacent and/or overlapping partial regions. Specifically, the contour line may run parallel to the displacement of the imaging device such that the row changes from column to column. The contour line may extend from the first partial region within the second partial region.

In case the multi-chamber plate is bent in a longitudinal direction, in particular z direction, the columns of the matrix of chambers represent equidistant contour lines. In this case, the contour line may be a straight contour line wherein the row remains the same along the contour line. If the orientation of one or both of the multi-chamber plate or the imaging device is adjusted such that one of the straight contour lines is observable, in particular focused, in both the first partial region and the second partial region, this contour line can be identified and can be used to match the first and second partial images.

As further used herein, the term "at least one contour line is observable" generally refers to a contour line that is one or more of visible, detectable, recognizable by the imaging device, in particular without changing the focal length of the imaging device. The contour line may be within a focus plane of the imaging device. Specifically, the contour line may be precisely focused and/or acceptably sharp. As used herein, the term "acceptably sharp" generally refers to a diameter of a circle of confusion of $0.05 \times 10^{-3}$ m or less, particularly of $0.025 \times 10^{-3}$ m or less and more particularly $0.01 \times 10^{-3}$ m or less. As outlined above, the flat element, and in particular the surface, may be bent and/or warped during thermal cycling such that deviations from the planar design occur. The contour line may be a sharp line or swathe through the bent and warped surface.

The method comprises forming at least one composite image from the first partial image and the second partial image by matching the first partial image and second partial image using the contour line. As used herein, the term "forming" generally refers to one or more of combining, stitching, joining, merging the first partial image and the second partial image into a composite image. The step of forming the composite image furthermore may comprise at least one cutting step, wherein overlapping regions are cut in one of the first or the second partial regions. As used herein, the term "composite image" generally refers to an image of the entire area of the multi-chamber plate covered and/or imaged by the imaging device which is composed of the partial images. The composite image may be formed such that all chambers and/or wells of the multi-chamber plate are comprised once within the composite image. In particular, none of the chambers is comprised twice. The composite image may be a combined image of the imaged partial regions. The matching of the first partial image and second partial image may comprise identifying at least one contour line observable in both of the partial images. Specifically identifying at least one contour line observable in both of the partial images which is focused. Furthermore, the matching may comprise comparing the partial images and stitching the partial images such that the composite image exhibits the at least one continuous contour line. As outlined above, the multi-chamber plate may comprise at least one array of chambers. Forming the composite image may comprise counting columns and/or rows of the array of chambers. Forming the composite image may be performed before reading out region by region every single chamber.

In the method at least one information about the displacement of one or both of the multi-chamber plate or the imaging device along the axis may be determined. As used herein, the term "information about a displacement" generally refers to an information about a coordinate on the axis, e.g. a coordinate on the x axis. The bent and/or warped surface can be mapped using at least one contour line. Due to its unevenness the multi-chamber plate may be outside a depth of focus range of the imaging device. By adjusting the orientation of one or both of the multi-chamber plate or the imaging device allows to have at least parts, in particular the contour line, of the partial image to be focused. The multi-chamber plate and/or the imaging device may be adjusted such that a contour line is observable, in particular focused, from the first end of the multi-chamber plate to the second end. The contour line may run parallel to the displacement of the imaging device such that the row changes from column to column. In case the multi-chamber plate being bent in a longitudinal direction, in particular z direction, the columns of the matrix of chambers represent equidistant contour lines. The partial regions may be imaged without changing the focal length of the imaging device. The partial images may be matched by using the sharp image of the at least one contour line. The method may allow to measure the exact amount of displacement by using the imaging device which, in particular continuously, monitors a movement of one or both of the multi-chamber plate or the imaging device by observing the movement of the chambers. By counting the columns and/or rows while displacing one or both of the imaging device and/or the multi-chamber plate without losing focus may allow determining the displacement of one or both of the multi-chamber plate or the imaging device along the axis, in particular a number of columns and/or rows, correctly. The method may allow determining the displacement of one or both of the multi-chamber plate or the imaging device along the axis without using fiducials and without using autofocus techniques.

The imaging device may have at least one focal length. In particular, the imaging device may comprise one or more lenses having at least one focal length. The focal length of the imaging device may be adjustable. For example, the imaging device may comprise an adjustable lens or lens system. The method may comprise adjusting a depth of focus of the imaging device. The adjustment of the depth of focus may be performed before imaging the partial regions. The adjustment of the depth of focus may be performed once. The depth of focus is unchanged during imaging the first and second partial regions.

As outlined above, the multi-chamber plate may comprise at least one array of chambers. The method may comprise at least one readout step. The readout step may comprise reading out a plurality of chambers, in particular the entire multi-chamber plate. The readout step may be performed after determining a displacement along the axis. The readout step may be performed after the formation of the composite image. The readout step may be performed using adjusting the focal length of the imaging device in order to bring other regions, in particular other chambers, into the focus. The readout step may comprise using autofocus techniques.

In a further aspect of the present disclosure, a multi-chamber plate analysis device is disclosed. As used herein, the term "multi-chamber plate analysis device" generally refers to an arbitrary device adapted to analyze at least one multi-chamber plate. The multi-chamber plate analysis device comprises at least one imaging device. The multi-chamber plate analysis device is adapted to displace the imaging device and the multi-chamber plate relative to each other along at least one axis. The imaging device is adapted to image at least one first partial image of at least one first partial region of the multi-chamber plate and at least one second partial image of at least one second partial region of the multi-chamber plate. The first partial region and the second partial region are one or both of adjacent or overlapping partial regions of the multi-chamber plate. The multi-chamber plate analysis device is adapted to adjust an orientation of one or both of the multi-chamber plate or the imaging device such that at least one contour line is observable in both the first partial region and the second partial region. The multi-chamber plate analysis device comprises at least one evaluation device, wherein the evaluation device is adapted to form at least one composite image from the first partial image and the second partial image by matching the first partial image and second partial image by using the contour line.

For details, options and definitions, reference may be made to the method as discussed above. Thus, specifically, the multi-chamber plate analysis device may be adapted to perform a method according to the present disclosure, such as according to one or more of the embodiments given above or given in further detail below.

As used herein, the term "evaluation device" generally refers to an arbitrary device adapted to form the at least one composite image, particularly by using at least one data processing device and, more particularly, by using at least one processor and/or at least one application-specific integrated circuit. Thus, as an example, the at least one evaluation device may comprise at least one data processing device having a software code stored thereon comprising a number of computer commands. The evaluation device may provide one or more hardware elements for performing one or more of the named operations and/or may provide one or more processors with software running thereon for performing one or more of the named operations.

The multi-chamber plate analysis device may comprise at least one multi-chamber plate holder adapted to receive the multi-chamber plate. The multi-chamber plate holder may be adapted to adjust the orientation of the multi-chamber plate, for example by tilting the multi-chamber plate holder. The multi-chamber plate holder may be adapted to displace the multi-chamber plate relative to the imaging device. The imaging device may comprise at least one optical system, wherein the optical system comprises at least one optical element selected from the group of: at least one detector; at least one lens; at least one lens system. The imaging device may be adapted to monitor, in particular continuously, a movement of the multi-chamber plate relative to the imaging device.

The present disclosure may allow one to correctly determine the displacement of one or both of the multi-chamber plate or the imaging device along the axis, in particular a number of columns and/or rows, by counting the columns and/or rows while displacing one or both of the imaging device and/or the multi-chamber plate without losing focus. The present disclosure may enable the determination of the displacement of one or both of the multi-chamber plate or the imaging device along the axis without using fiducials and without using autofocus techniques.

Summarizing the ideas of the present disclosure, the following items are specifically disclosed:

Embodiment 1: A method for analyzing a multi-chamber plate, wherein the method comprises the following steps:

displacing at least one imaging device and the multi-chamber plate relative to each other along at least one axis;

imaging at least one first partial image of at least one first partial region of the multi-chamber plate and at least one second partial image of at least one second partial region of the multi-chamber plate, wherein the first partial region and the second partial region are one or both of adjacent or overlapping partial regions of the multi-chamber plate;

adjusting an orientation of one or both of the multi-chamber plate or the imaging device such that at least one contour line is observable in both the first partial region and the second partial region;

forming at least one composite image from the first partial image and the second partial image by matching the first partial image and second partial image by using the contour line.

Embodiment 2: The method according to the preceding embodiment, wherein in the method at least one information about a displacement of one or both of the multi-chamber plate or the imaging device along the axis is determined.

Embodiment 3: The method according to any one of the preceding embodiments, wherein the contour line is within a focus plane of the imaging device.

Embodiment 4: The method according to any one of the preceding embodiments, wherein the multi-chamber plate comprises at least one array of chambers.

Embodiment 5: The method according to the preceding embodiment, wherein forming the composite image comprises counting columns and/or rows of the array of chambers.

Embodiment 6: The method according to any one of the preceding embodiments, wherein the multi-chamber plate has a first end and a second end, wherein the contour line extends from the first end to the second end.

Embodiment 7: The method according to any one of the preceding embodiments, wherein the imaging device comprises at least one sensor having at least one sensor surface, wherein adjusting the orientation of the image device and/or of the multi-chamber plate comprises adjusting a spatial orientation of the sensor surface and the multi-chamber plate relative to each other.

Embodiment 8: The method according to the preceding embodiment, wherein the multi-chamber plate is tilted within a depth of field of the imaging device.

Embodiment 9: The method according to any one of the preceding embodiments, wherein the imaging device has a field of view smaller than an extension of the multi-chamber plate along the axis.

Embodiment 10: The method according to any one of the preceding embodiments, wherein the imaging device comprises at least one optical system, wherein the optical system comprises at least one optical element selected from the group of: at least one detector; at least one lens; at least one lens system.

Embodiment 11: The method according to any one of the preceding embodiments, wherein the imaging device is adapted to monitor a movement of the multi-chamber plate along the axis.

Embodiment 12: The method according to any one of the preceding embodiments, wherein the method comprises imaging subsequently partial regions of the multi-chamber plate.

Embodiment 13: The method according to any one of the preceding embodiments, wherein the imaging device has at least one focal length.

Embodiment 14: The method according to the preceding embodiment, wherein the focal length of the imaging device is adjustable.

Embodiment 15: The method according to any one of the two preceding embodiments, wherein the method comprises adjusting a depth of focus of the imaging device.

Embodiment 16: The method according to any one the preceding embodiments, wherein the multi-chamber plate comprises at least one array of chambers, wherein the method comprises at least one readout step, wherein the readout step comprises reading out a plurality of chambers, wherein the readout step is performed after the formation of the composite image.

Embodiment 17: A multi-chamber plate analysis device, wherein the multi-chamber plate analysis device comprises at least one imaging device, wherein the multi-chamber plate analysis device is adapted to displace the imaging device and the multi-chamber plate relative to each other along at least one axis, wherein the imaging device is adapted to image at least one first partial image of at least one first partial region of the multi-chamber plate and at least one second partial image of at least one second partial region of the multi-chamber plate, wherein the first partial region and the second partial region are one or both of adjacent or overlapping partial regions of the multi-chamber plate, wherein the multi-chamber plate analysis device is adapted to adjust an orientation of one or both of the multi-chamber plate or the imaging device such that at least one contour line is observable in both the first partial region and the second partial region, wherein the multi-chamber plate analysis device comprises at least one evaluation device, wherein the evaluation device is adapted to form at least one composite image from the first partial image and the second partial image by matching the first partial image and second partial image by using the contour line.

Embodiment 18: The multi-chamber plate analysis device according to the preceding embodiment, wherein the multi-chamber plate analysis device is adapted to perform a method according to any one of the preceding embodiments referring to a method.

Embodiment 19: The multi-chamber plate analysis device according to any one of the preceding embodiments referring to a multi-chamber plate analysis device, wherein the multi-chamber plate analysis device comprises at least one multi-chamber plate holder adapted to receive the multi-chamber plate.

Embodiment 20: The multi-chamber plate analysis device according to the preceding embodiment, wherein the multi-chamber plate holder is adapted to adjust the orientation of the multi-chamber plate.

Embodiment 21: The multi-chamber plate analysis device according to any one of the two preceding embodiments, wherein the multi-chamber plate holder is adapted to displace the multi-chamber plate relative to the imaging device.

Embodiment 22: The multi-chamber plate analysis device according to any one of the preceding embodiments referring to a multi-chamber plate analysis device, wherein the imaging device comprises at least one optical system, wherein the optical system comprises at least one optical element selected from the group of: at least one detector; at least one lens; at least one lens system.

Embodiment 23: The multi-chamber plate analysis device according to the preceding embodiment, wherein the imaging device is adapted to monitor a movement of the multi-chamber plate.

EXAMPLE

Figure 1:
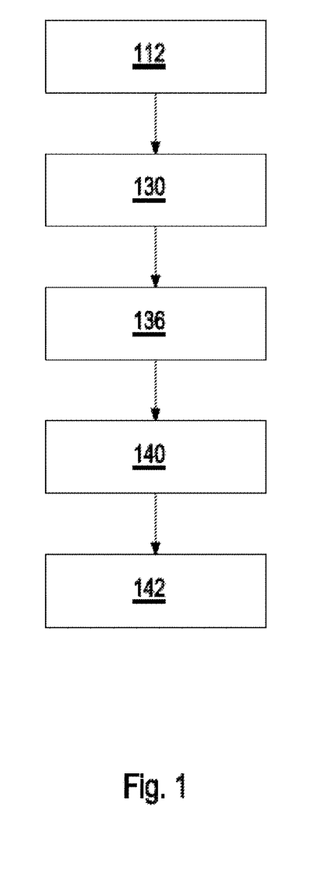
FIG. 1 shows an embodiment of a method for analyzing a multi-chamber plate according to the present disclosure.
Figure 2:
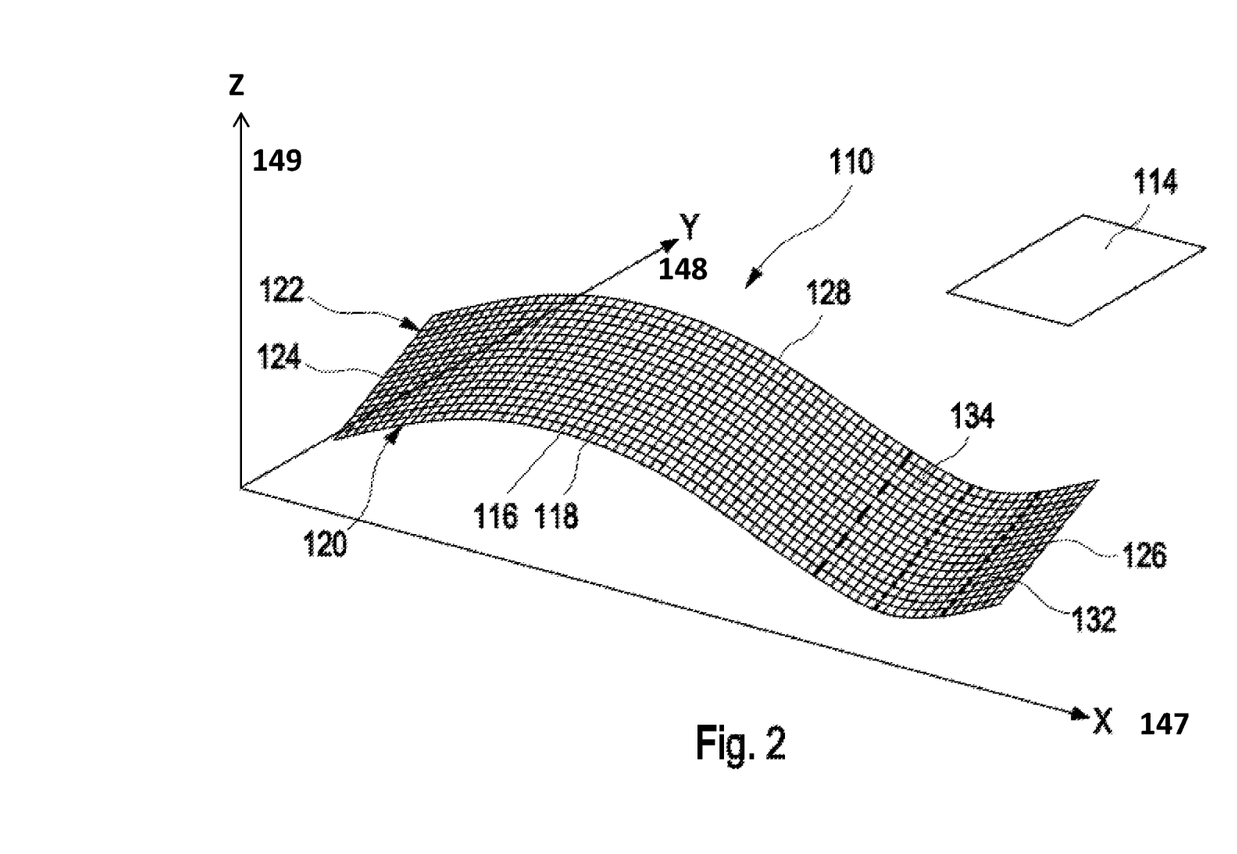
FIG. 2 shows a first embodiment of an orientation of the multi-chamber plate and an imaging device.

In FIG. 1, an embodiment of a method for analyzing a multi-chamber plate 110 according to the present disclosure is shown. The method comprises displacing 112 at least one imaging device 114 and the multi-chamber plate 110 relative to each other along at least one axis. An embodiment of a multi-chamber plate 110 and imaging device 114 is shown in FIG. 2. The multi-chamber plate 110 may comprise a plurality of wells, also denoted as chambers. The multi-chamber plate 110 may be a micro-well plate or a nano-well plate. The multi-chamber plate 110 may comprise at least one array 116 of chambers 118. In particular, the multi-chamber plate may comprise an array of wells. The chambers 118 may comprise chamber walls. For example, a well may have four chamber walls and may have a rectangular or quadratic base area. However, other base areas are possible. The multi-chamber plate 110 may comprise a matrix with columns 120 and rows 122 formed by chamber walls. The matrix specifically may be or may comprise a rectangular matrix having one or more rows 122 and one or more columns 120. The rows 122 and columns 120 specifically may be arranged in a rectangular fashion. However, other arrangements are feasible, such as nonrectangular arrangements.

The imaging device 114 and/or the multi-chamber plate 110 may be displaced along one axis, or along more than one axis. The multi-chamber plate may have a first end 124 and a second end 126. An x direction may be defined as a direction from the first end 124 to the second end 126. A length of the multi-chamber plate may be a distance from the first end 124 to the second end 126. Particularly, one or both of the imaging device 114 and the multi-chamber plate 110 may be displaced relative to each other along one axis, in particular along the x-axis 147. A y-axis 148 may be perpendicular to the x-axis, in particular along a width of the multi-chamber plate 110. A z-axis 149 may be perpendicular to an xy plane.

The multi-chamber plate 110 may comprise an essentially flat element 128 comprising the plurality of chambers 118. The chambers 118 may be located in one and the same plane. The essentially flat element 128 may comprise a surface. The essentially flat element 128 may be planar within the xy plane, with a tolerance of e.g. ±20° or less, particularly a tolerance of ±10° or less, more particularly a tolerance of ±5° or less. In particular, the surface of the essentially flat element may be planar within the xy plane, with a tolerance of e.g. ±20° or less, particularly a tolerance of ±10° or less, more particularly a tolerance of ±5° or less. The flat element 128, and in particular the surface, may be bent and/or warped during thermal cycling such that deviations from the planar design occur.

The imaging device 114 may comprise at least one sensor, in particular at least one optical sensor. The sensor may be formed as a unitary, single device or as a combination of several devices. The imaging device 114 may comprise at least one optical system. The optical system may comprise at least one optical element selected from the group of: at least one detector, at least one lens; at least one lens system. The imaging device 114 may be adapted to monitor a movement of the multi-chamber plate along the axis, in particular continuously. For example, the imaging device 114 may comprise a camera, e.g. a video-camera.

The method comprises imaging 130 at least one first partial image of at least one first partial region 132 of the multi-chamber plate 110 and at least one second partial image of at least one second partial region 134 of the multi-chamber plate 110. The imaging device 114 may have a field of view smaller than an extension of the multi-chamber plate 110 along the axis. The extension of the multi-chamber plate 110 may be two, three or more times larger than the field of view such that the imaging device 114 may be adapted to image parts of the multi-chamber plate 110. Partial regions 132, 134, in particular a length in the x direction, may be defined by the displacement and the field of view of the imaging device 114. Each partial region may have a center, wherein the centers of the first partial region 132 and the second partial region 134 have different x-coordinates. The first partial region 132 and the second partial region 134 may be adjacent subsequent regions along the x axis. The first partial region 132 and the second partial region 134 may be neighboring partial regions. The first partial region 132 and the second partial region 134 may overlap. The first and second partial regions 132, 134 may be imaged without changing a focal length of the imaging device 114. The method may comprise imaging subsequent partial regions of the multi-chamber plate 110. The method may comprise imaging the entire multi-chamber plate 110. The imaging device 114 may be adapted to image the entire multi-chamber plate 110 by imaging a plurality of partial regions.

Figure 3:
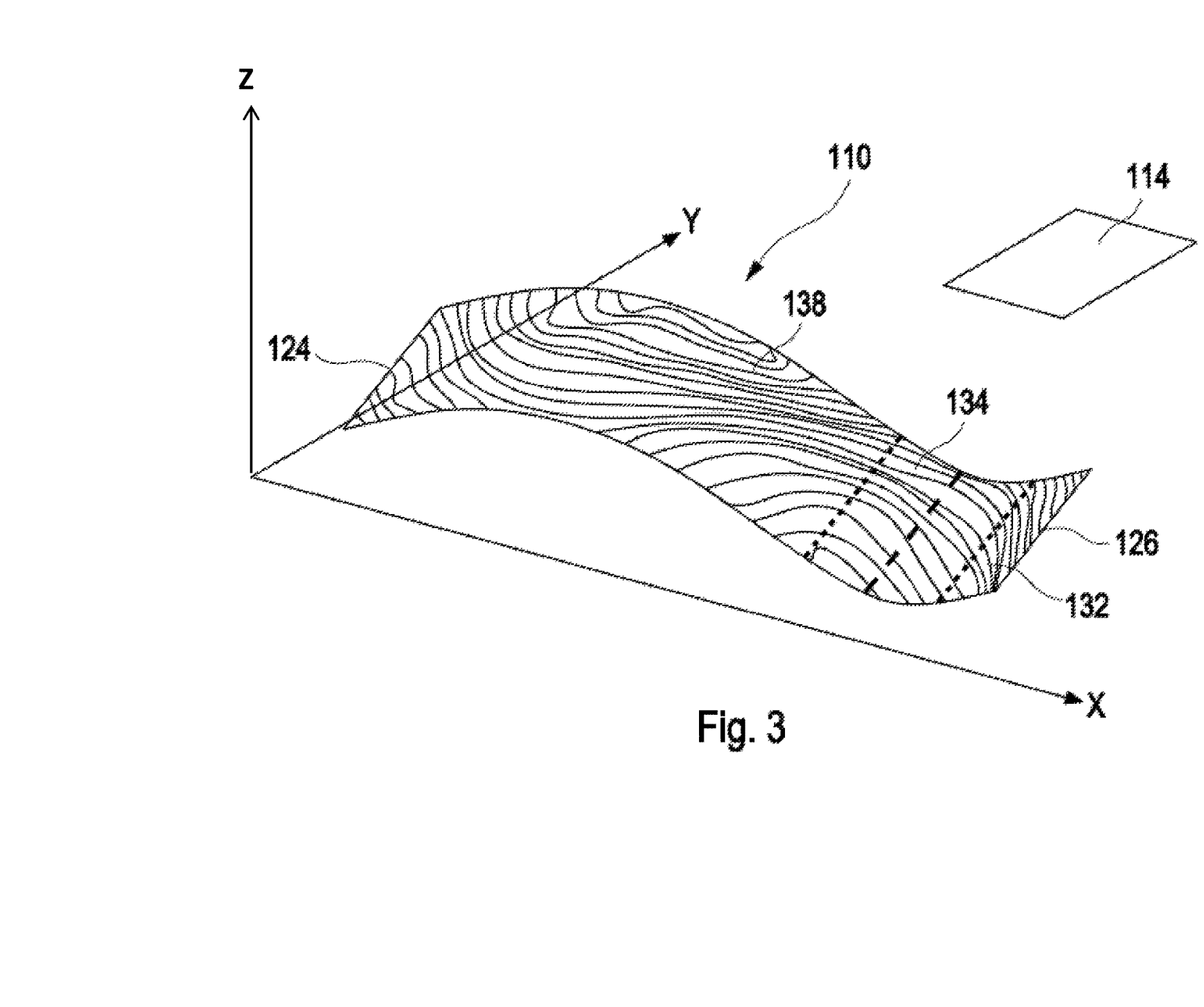
FIG. 3 shows contour lines observable in the multi-chamber plate.

The method comprises adjusting 136 the orientation of one or both of the multi-chamber plate 110 or the imaging device 114 such that at least one contour line 138 is observable in both the first partial region 132 and the second partial region 134. FIG. 3 shows contour lines observable in the multi-chamber plate 110. The adjusting step 136 may comprise one or more of aligning, shifting, tilting, changing, twisting the orientation of one or both of the multi-chamber plate 110 or the imaging device 114. In FIGS. 2 to 5 the first embodiment of an orientation, wherein one or both of the multi-chamber plate 110 or the imaging device 114 are tilted, is shown. The imaging device 114 may comprise at least one sensor having at least one sensor surface. Adjusting the orientation of the image device 114 and/or of the multi-chamber plate 110 may comprise adjusting a spatial orientation of the sensor surface and the multi-chamber plate 110 relative to each other, in particular changing at least one spatial angle between the sensor surface and the multi-chamber plate 110. For example, the multi-chamber plate 110 and/or the imaging device 114 may be tilted relative to each other by no more than 20°, particularly of no more than 10°, more particularly of no more than 5°.

For example, the multi-chamber plate 110 may be tilted within a depth of field of the imaging device 114. The multi-chamber plate may be tilted precisely within and slightly beyond the depth of field. Additionally or alternatively, the imaging device 114 may be tilted such that the multi-chamber plate 110 is precisely within and slightly beyond the depth of field. The multi-chamber plate 110 may be tilted and/or may be within the depth of field of the imaging device 114 such that at least one contour line may be precisely focused and/or acceptably sharp.

Figure 4:
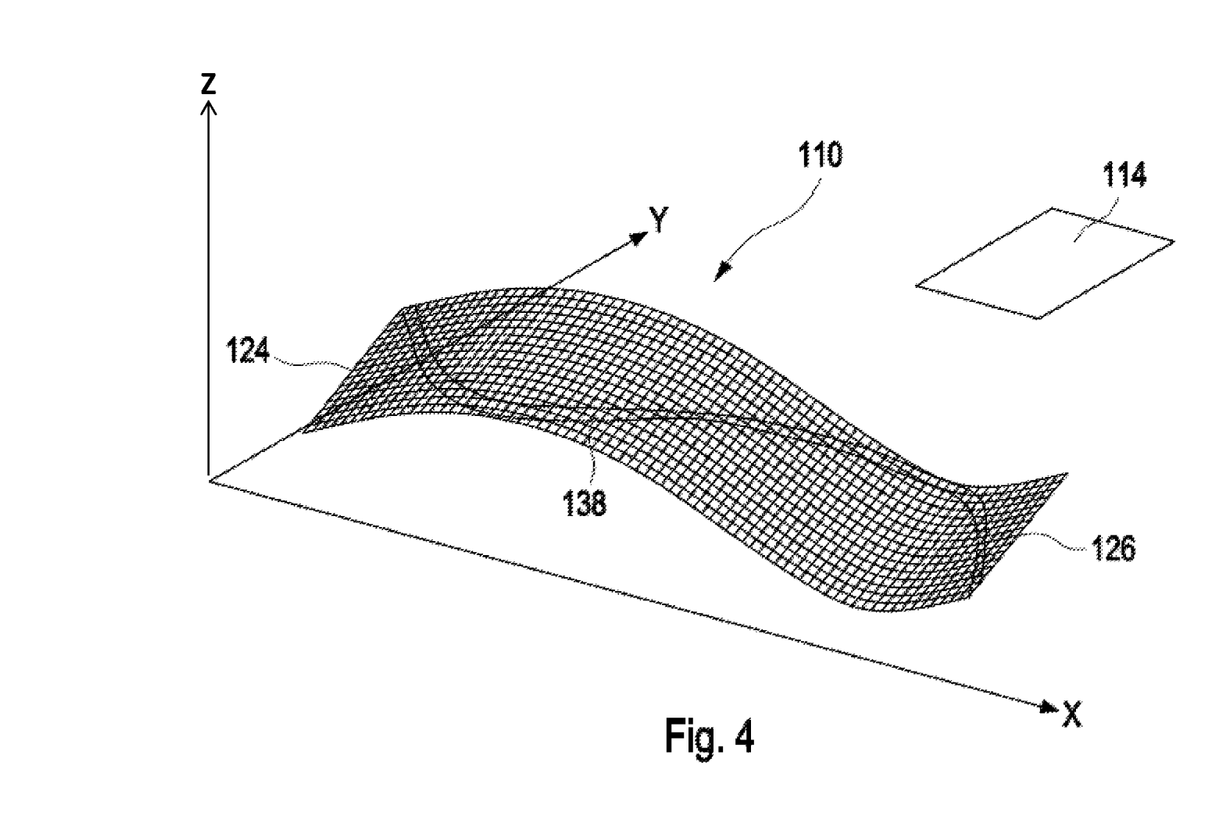
FIG. 4 shows a development of one exemplary contour line in the multi-chamber plate.
Figure 5:
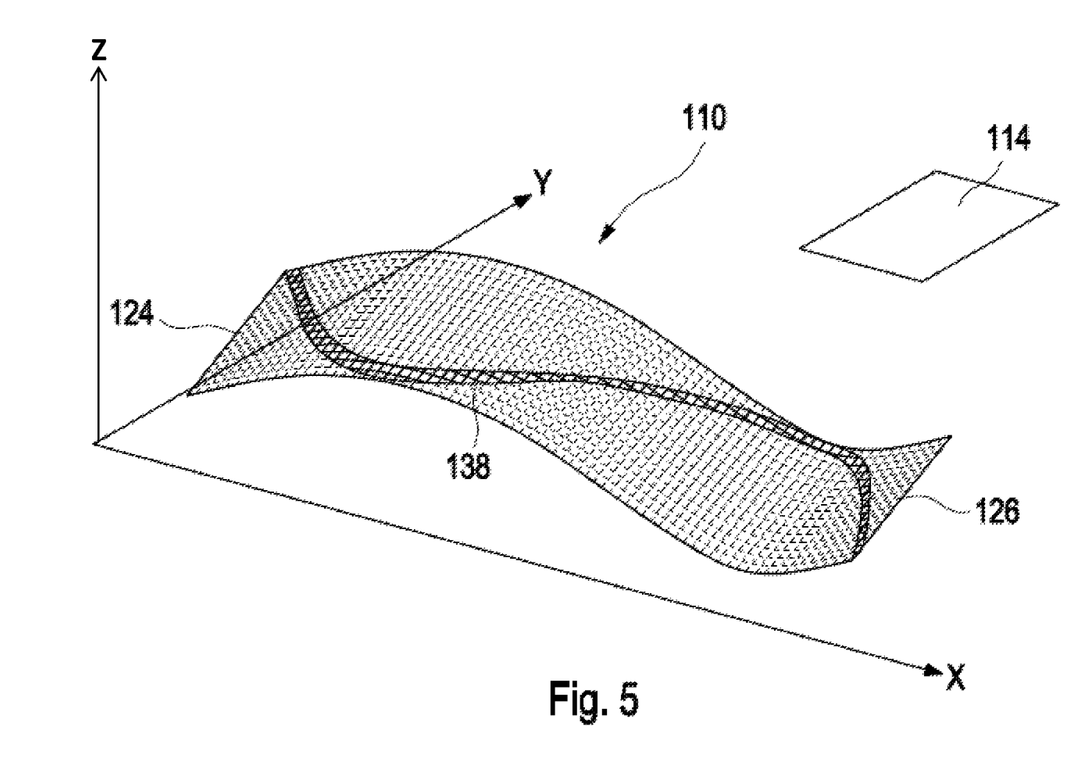
FIG. 5 shows a sharp image of the exemplary contour line.

In FIGS. 3 to 5, the contour lines may be curved contour lines. The contour line 138 may extend from the first end 124 to the second end 126. FIG. 4 shows a development of the contour line 138 in the multi-chamber plate extending from the first end 124 to the second end 126. The contour line 138 may be continuous. In particular, the contour line 138 may be continuous in a transition or a transition region or an overlapping region of the first partial region 132 and second partial region 134. Specifically, the contour line 138 may have no jumps in the transition region or the overlapping region of the first partial region 132 and second partial region 134. The contour line 138 may extend in both the first partial region 132 and the second partial region 134. The contour line 138 may extend in two adjacent and/or overlapping partial regions. Specifically, the contour line 138 may run parallel to the displacement of the imaging device 114 such that the row 122 changes from column 120 to column 120. The contour line 138 may extend from the first partial region 132 within the second partial region 134.

FIG. 5 shows a sharp image of the exemplary contour line 138. The contour line may be within a focus plane of the imaging device. Specifically, the contour line may be precisely focused and/or acceptably sharp. As outlined above, the flat element, and in particular the surface, may be bent and/or warped during thermal cycling such that deviations from the planar design occur. The contour line may be a sharp line or swathe through the bent and warped surface. The sharp image of the contour line 138 along the multi-chamber plate 110 may provide the possibility to accurately count the columns 120 of the chambers 118. As can be seen in FIG. 5, other regions of the multi-chamber plate 110 may be out of focus.

Figure 6:
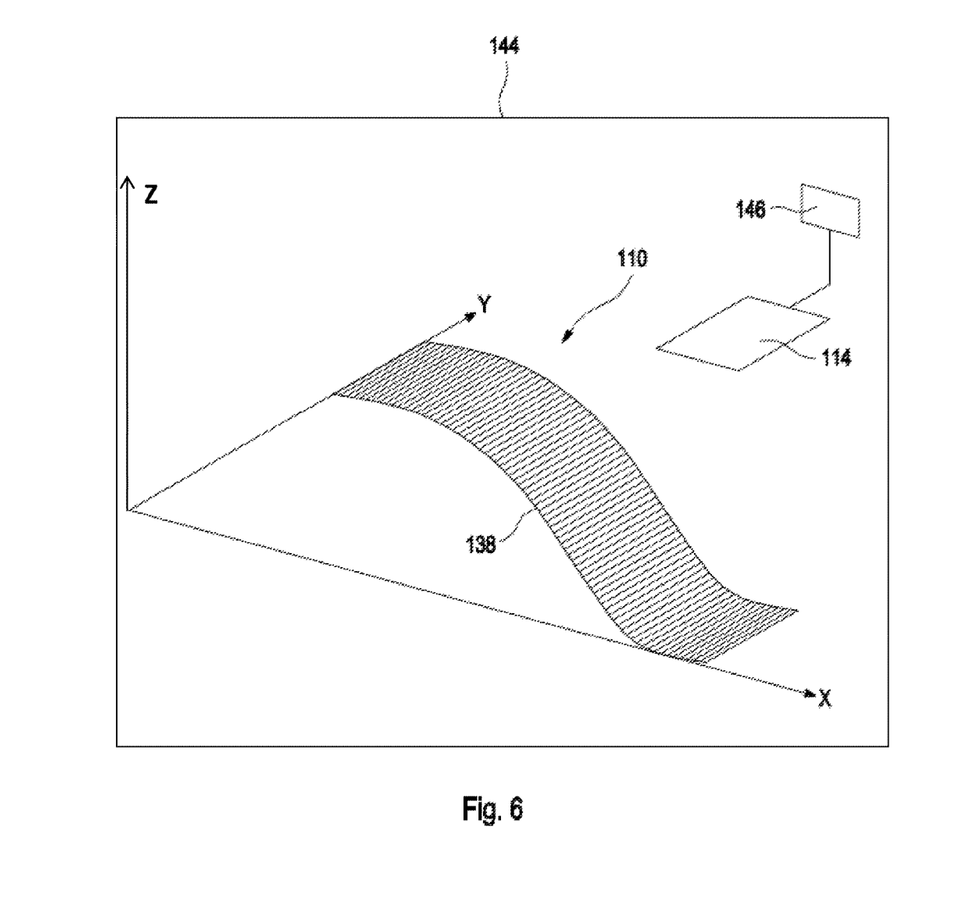
FIG. 6 shows an embodiment of a multi-chamber plate analysis device according to the present disclosure and a second embodiment of the orientation of the multi-chamber plate and the imaging device.

FIG. 6 shows a second embodiment of the orientation of the multi-chamber plate 110 and the imaging device 114, wherein the multi-chamber plate 110 is bent in only a longitudinal direction, in particular z direction. In this case, the columns 120 of the matrix of chambers 118 represent equidistant contour lines 138. In this case, the contour line 138 may be a straight contour line wherein the row 122 remains the same along the contour line 138. If the orientation of one or both of the multi-chamber plate 110 or the imaging device 114 is adjusted such that one of the straight contour line 138 is observable, in particular focused, in both the first partial region 132 and the second partial region 134, this contour line 138 can be identified and can be used to match the first and second partial images.

The method comprises forming 140 at least one composite image from the first partial image and the second partial image by matching the first partial image and second partial image by using the contour line 138. The step of forming 140 may comprise one or more of combining, stitching, joining, merging the first partial image and the second partial image into a composite image. The step of forming 140 the composite image furthermore may comprise at least one cutting step, wherein overlapping regions are cut in one of the first or the second partial regions. The composite image may be formed such that all chambers 118 of the multi-chamber plate 110 are comprised once within the composite image. In particular, none of the chambers 118 is comprised twice. The composite image may be a combined image of the imaged partial regions 132, 134. The matching of the first partial image and second partial image may comprise identifying at least one contour line 138 observable in both of the partial images, specifically identifying at least one contour line 138 observable in both of the partial images which is focused. Furthermore, the matching may comprise comparing the partial images and stitching the partial images such that the composite image exhibits the at least one continuous contour line 138. Forming the composite image may comprise counting columns 120 and/or rows 122 of the array of chambers 118. Forming the composite image may be performed before reading out region by region every single chamber 118.

In the method at least one information about the displacement of one or both of the multi-chamber plate 110 or the imaging device 114 along the axis may be determined. The bent and/or warped surface of the multi-chamber plate 110 can be mapped using at least one contour line 138. Due to its unevenness, the multi-chamber plate 110 may be outside a depth of focus range of the imaging device 114. By adjusting the orientation of one or both of the multi-chamber plate 110 or the imaging device 114 allows to have at least parts, in particular the contour line 138, of the partial image to be focused. The multi-chamber plate 110 and/or the imaging device 114 may be adjusted such that a contour line 138 is observable, in particular focused, from one first end 124 of the multi-chamber plate to the second end 126. The contour line 138 may run parallel to the displacement of the imaging device 114 such that the row 122 changes from column 120 to column 120. In case of the multi-chamber plate 110 being bent in a longitudinal direction, in particular z direction, the columns 120 of the matrix of chambers represent equidistant contour lines 138. The partial regions 132, 134 may be imaged without changing the focal length of the imaging device 114. The partial images 132, 134 may be matched by using the sharp image of said contour line 138. The method may allow to measure the exact amount of displacement by using the imaging device 114 which, in particular continuously, monitors a movement of one or both of the multi-chamber plate 110 or the imaging device 114 by observing the movement of the chambers 118. By counting the columns 120 and/or rows 122 while displacing one or both of the imaging device 114 and/or the multi-chamber plate 110 without losing focus may allow determining the displacement of one or both of the multi-chamber plate 110 or the imaging device 114 along the axis, in particular a number of columns 120 and/or rows 122, correctly. The method may allow determining the displacement of one or both of the multi-chamber plate 110 or the imaging device 114 along the axis without using fiducials and without using autofocus techniques.

The method may comprise at least one readout step 142. The readout step 142 may comprise reading out a plurality of chambers 118, in particular the entire multi-chamber plate 110. The readout step 142 may be performed after determining a displacement along the axis. The readout step 142 may be performed after the formation of the composite image. The readout step 142 may be performed using adjusting the focal length of the imaging device 114 in order to bring other regions, in particular other chambers 118, into the focus. The readout step 142 may comprise using autofocus techniques.

FIG. 6 further shows a schematic representation of an exemplary embodiment of a multi-chamber plate analysis device 144. The multi-chamber plate analysis device 144 comprises the imaging device 114. The multi-chamber plate analysis device 144 is adapted to displace the imaging device 114 and the multi-chamber plate 110 relative to each other along at least one axis. The imaging device 114 is adapted to image the at least one first partial image of the at least one first partial region 132 of the multi-chamber plate 110 and the at least one second partial image of the at least one second partial region 134 of the multi-chamber plate 110. The first partial region 132 and the second partial region 134 are one or both of adjacent or overlapping partial regions of the multi-chamber plate 110. The multi-chamber plate analysis device is adapted to adjust an orientation of one or both of the multi-chamber plate or the imaging 144 device such that the at least one contour line 138 is observable in both the first partial region 132 and the second partial region 134. The multi-chamber plate analysis device comprises at least one evaluation device 146, wherein the evaluation device 146 is adapted to form at least one composite image from the first partial image and the second partial image by matching the first partial image and second partial image by using the contour line 138.

The at least one evaluation device 146 may comprise at least one data processing device having a software code stored thereon comprising a number of computer commands. The evaluation device 146 may provide one or more hardware elements for performing one or more of the named operations and/or may provide one or more processors with software running thereon for performing one or more of the named operations.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims.

Various publications are cited herein, the disclosures of which are incorporated by reference in their entireties.

REFERENCE NUMERALS 110 multi-chamber plate
112 displacing
114 imaging device
116 array
118 chambers
120 column
122 row
124 first end
126 second end
128 essential flat element
130 imaging
132 first partial region
134 second partial region
136 adjusting
138 contour line
140 forming
142 readout step
144 multi-chamber plate analysis device
146 evaluation device

The invention claimed is:

1. A method for analyzing a multi-chamber plate, wherein the method comprises the following steps:
    a) displacing at least one imaging device and the multi-chamber plate relative to each other along at least one axis;
    b) imaging at least one first partial image of at least one first partial region of the multi-chamber plate and at least one second partial image of at least one second partial region of the multi-chamber plate, wherein the first partial region and the second partial region are one or both of adjacent or overlapping partial regions of the multi-chamber plate;
    c) adjusting an orientation of one or both of the multi-chamber plate or the imaging device such that at least one contour line is observable in both the first partial region and the second partial region;
    d) forming at least one composite image from the first partial image and the second partial image by matching the first partial image and second partial image by using the contour line.

2. The method of claim 1, wherein the method further comprises determining at least one information about a displacement of one or both of the multi-chamber plate or the imaging device along the axis.

3. The method of claim 1, wherein the at least one contour line is positioned within a focus plane of the imaging device.

4. The method of claim 1, wherein the multi-chamber plate comprises at least one array of chambers and the step of forming the at least one composite image comprises counting columns and/or rows of the array of chambers.

5. The method of claim 1, wherein the multi-chamber plate has a first end and a second end, wherein the contour line extends from the first end to the second end.

6. The method of claim 1, wherein the imaging device comprises at least one sensor having at least one sensor surface and the step of adjusting the orientation of the image device and/or of the multi-chamber plate comprises adjusting a spatial orientation of the sensor surface and the multi-chamber plate relative to each other.

7. The method of claim 1, wherein the multi-chamber plate is tilted within a depth of field of the imaging device.

8. The method of claim 1, wherein the imaging device has a field of view smaller than an extension of the multi-chamber plate along the axis.

9. The method of claim 1, wherein the imaging device comprises at least one optical system, wherein the optical system comprises at least one optical element selected from the group of: at least one detector; at least one lens; at least one lens system.

10. The method of claim 1, wherein the method further comprises monitoring, via the imaging device, a movement of the multi-chamber plate along the axis.

11. The method of claim 1, wherein the method comprises imaging subsequently partial regions of the multi-chamber plate.

12. The method of claim 1, wherein the multi-chamber plate comprises at least one array of chambers, wherein the method comprises reading out a plurality of chambers after the forming the composite image.

* * * * *